(12) United States Patent
Shi et al.

(10) Patent No.: US 12,343,017 B2
(45) Date of Patent: Jul. 1, 2025

(54) DISASSEMBLY-AND-ASSEMBLY-FREE FLUSHABLE CLAMP APPLIER

(71) Applicant: HANGZHOU SUNSTONE TECHNOLOGY CO., LTD., Hangzhou (CN)

(72) Inventors: Lei Shi, Hangzhou (CN); Weijian Dai, Hangzhou (CN); Yanli Ma, Hangzhou (CN)

(73) Assignee: HANGZHOU SUNSTONE TECHNOLOGY CO., LTD., Hangzhou (CN)

( * ) Notice: Subject to any disclaimer, the term of this patent is extended or adjusted under 35 U.S.C. 154(b) by 654 days.

(21) Appl. No.: 17/304,919

(22) Filed: Jun. 28, 2021

(65) Prior Publication Data
US 2021/0322021 A1 Oct. 21, 2021

Related U.S. Application Data

(63) Continuation of application No. PCT/CN2019/118744, filed on Nov. 15, 2019.

(30) Foreign Application Priority Data

Dec. 29, 2018 (CN) .......................... 201811634459.1

(51) Int. Cl.
  *A61B 17/128* (2006.01)
  *A61B 17/122* (2006.01)
  *A61B 17/00* (2006.01)

(52) U.S. Cl.
  CPC .......... *A61B 17/128* (2013.01); *A61B 17/122* (2013.01); *A61B 2017/00367* (2013.01)

(58) Field of Classification Search
  CPC ................ A61B 17/128; A61B 17/122; A61B 2017/00367; A61B 2090/0813; A61B 17/1285
  See application file for complete search history.

(56) References Cited

U.S. PATENT DOCUMENTS 4,938,408 A * 7/1990 Bedi .................... A61B 17/072
                                              227/19
5,578,052 A * 11/1996 Koros ................ A61B 18/1445
                                              606/174
(Continued)

FOREIGN PATENT DOCUMENTS

CN       201469342 U      5/2010
CN       202568368 U      12/2012
(Continued)

OTHER PUBLICATIONS

"International Application No. PCT/CN2019/118744, International Search Report and Written Opinion mailed Feb. 26, 2020", (Feb. 26, 2020), 11 pgs.

*Primary Examiner* — Ryan J. Severson
(74) *Attorney, Agent, or Firm* — Schwegman Lundberg & Woessner, P.A.

(57) ABSTRACT

A disassembly-free and flushable clip applier includes: a fixing handle and a triggering handle, the fixing handle being hinged with the triggering handle, the fixing handle being provided with a locking key; an end of the cavity tube being provided with a mounting head which is configured for detachably connecting the ligating clip; a turning mechanism sleeved at the other end of the cavity tube and rotatably connected with the fixing handle through a rolling ball, the turning mechanism being provided with a flushing valve which is communicated with the cavity tube for flushing; and a thimble axially infixed into the cavity tube and reciprocating along an axial direction of the cavity tube. The clip applier does not need disassembly and reassembly during cleaning and disinfection and prevent a risk of accidental touching triggering when the ligating clip is being assembled and fails to reach a clipping position.

8 Claims, 7 Drawing Sheets

(56) References Cited

U.S. PATENT DOCUMENTS

| | | | |
|---|---|---|---|
| 2008/0004637 A1 | 1/2008 | Klassen et al. | |
| 2010/0004599 A1* | 1/2010 | Zhou | A61B 17/3498 604/167.04 |
| 2012/0265242 A1* | 10/2012 | Matthew | A61B 17/29 606/208 |
| 2013/0261642 A1* | 10/2013 | Willett | A61B 90/03 606/143 |
| 2016/0113655 A1* | 4/2016 | Holsten | A61B 17/1285 606/143 |
| 2016/0135817 A1* | 5/2016 | Kerboul | A61B 17/1611 606/83 |
| 2016/0151071 A1* | 6/2016 | Tokarz | A61B 17/1285 606/143 |
| 2018/0235637 A1 | 8/2018 | Xu et al. | |
| 2019/0133596 A1* | 5/2019 | Brodaczewski | A61B 17/2909 |
| 2019/0216464 A1* | 7/2019 | Baril | A61B 17/2909 |

FOREIGN PATENT DOCUMENTS

| | | |
|---|---|---|
| CN | 202908767 U | 5/2013 |
| CN | 108348259 A | 7/2018 |
| CN | 109480951 A | 3/2019 |
| CN | 209629748 U | 11/2019 |
| WO | WO-2020134679 A1 | 7/2020 |

\* cited by examiner

DISASSEMBLY-AND-ASSEMBLY-FREE FLUSHABLE CLAMP APPLIER

CROSS-REFERENCE TO RELATED APPLICATIONS

This application is a continuation of International Application No. PCT/CN2019/118744 filed 15 Nov. 2019, which claims the benefit of priority to Chinese Application No. 201811634459.1, filed 29 Dec. 2018, the benefit of priority of each of which is claimed herein and which applications are hereby incorporated by reference herein in their entirety.

TECHNICAL FIELD

The disclosure relates to the technical field of medical instruments, and to a disassembly-free and flushable clip applier.

BACKGROUND ART

In a surgery, a ligating clip is often used to clip blood vessels and tissues of human body to stop bleeding and cut off a blood flow; when the ligating clip is used, it is necessary to use an applying tool to assist in occluding the blood vessels and tissues. Various components of an existing clip applying tool are required to be disassembled, cleaned and disinfected first after use, and then reassembled, packaged and disinfected for a later use. This whole process is tedious and increases working intensity and skill requirements of medical workers; moreover, damage, missing, mixed assembly and wrong assembly of parts can be easily caused in frequent disassembly, assembly and cleaning, resulting in an abnormal use of the clip applying tool. Furthermore, if a fault is discovered during an operation, a treatment accident may be caused. In addition, the clip applying tool is used as an auxiliary piece in combination with the ligating clip, and the existing clip applying tool lacks an action protection during this combined use, which easily results in damage to the ligating clip due to inadvertently touching a triggering mechanism in advance when the ligating clip is being assembled and fails to reach a clipping position, resulting in damage or scrapping of the ligating clip and thus an operation delay, which is unfavorable to health of patients.

SUMMARY

In view of above problems, the disclosure provides a disassembly-free and flushable clip applier, which provides perfect functions and convenient use and does not need disassembly and reassembly during cleaning and disinfection, thereby reducing working intensity and skill requirements of medical workers, avoiding damage, missing, mixed assembly and wrong assembly of parts caused due to frequent disassembly, assembly, cleaning and disinfection, and preventing a risk of accidental touching triggering when the ligating clip is being assembled and fails to reach a clipping position.

A technical scheme adopted in the disclosure is as follows. A disassembly-free and flushable clip applier is connected with a ligating clip and used for auxiliary application of the ligating clip, and is characterized in that it includes: a fixing handle and a triggering handle, the fixing handle being hinged with the triggering handle; a cavity tube, a front end of the cavity tube being provided with a mounting head which is configured for detachably connecting the ligating clip, a diameter of a tail end of the cavity tube being larger than a diameter of the front end of the cavity tube; a turning mechanism sleeved at the tail end of the cavity tube and rotatably connected with the fixing handle through a rolling ball, the turning mechanism being provided with a flushing valve which is communicated with the cavity tube for flushing; and a thimble axially infixed into the cavity tube and reciprocating along an axial direction of the cavity tube, the thimble including a tip and a tail, the tail being connected with the triggering handle and the tip being configured for pushing the ligating clip mounted on the mounting head of the cavity tube to move.

In an embodiment of the present disclosure, a first cavity and a second cavity are provided in the fixing handle. The first cavity is communicated with the second cavity, the triggering handle is arranged in the first cavity and hinged with the fixing handle through a joint screw; and the second cavity is communicated with the cavity tube for resetting the thimble and the tail end of the second cavity is screwed with a back cover.

In an embodiment of the present disclosure, the tail end of the cavity tube is provided with a pin hole and the fixing handle is provided with a rolling ball groove and a pin groove. An inner wall of the cavity tube is matched with the rolling ball groove through the rolling ball to realize a 360° rotation, and the cavity tube is axially limited by matching a pin with the pin groove.

In an embodiment of the present disclosure, the thimble further includes a needle bar and a resetting spring. An end of the needle bar is connected with the tip through a coaxial positioning structure attached to the inner wall of the cavity tube so that the tip is in a central position of the cavity tube. The other end of the needle bar is connected with the tail. A steel ring is sleeved on an outer side of the needle bar and a spring limiter is provided on an inner cavity surface of the cavity tube. The steel ring abuts against the spring limiter of the cavity tube for limiting. The resetting spring is sleeved on the needle bar, and an end of the resetting spring abuts against the tail and the other end of the resetting spring abuts against the steel ring for resetting the thimble.

In an embodiment of the present disclosure, the clip applier further includes a locking key. Two sides of the fixing handle are provided with locking key holes mutually communicated with each other. The locking key is movably arranged in the locking key holes, the fixing handle is provided with a key position spring for limiting unlocking and locking positions of the locking key. The locking key is provided with a locker and the triggering handle is provided with a lock hole, and the locker is matched with the lock hole for controlling a rotation of the triggering handle.

In an embodiment of the present disclosure, the fixing handle further includes a crook stop, which is arranged on a side of the fixing handle away from the triggering handle and is configured for a nonskid limiting of a crook of a palm during holding.

In an embodiment of the present disclosure, the clip applier further includes a protective cover which is detachably arranged on the flushing valve and is made of silica gel.

In an embodiment of the present disclosure, a plurality of ridges are circumferentially provided on an outer side of the turning mechanism for a single-finger dialing rotation.

In an embodiment of the present disclosure, a connection mode of the cavity tube with the ligating clip is a spring-snap connection or a screwing-snap connection.

In an embodiment of the present disclosure, an end of the triggering handle away from the thimble is provided with an annular force applying part for stably applying a force by a finger and preventing the clip applier from slipping from the hand during use.

The clip applier provided by the disclosure has beneficial effects that during use, the fixing handle is held and the triggering handle is buckled by fingers, the thimble can be driven to move in the cavity tube by the triggering handle, thereby driving the ligating clip connected with the cavity tube to move and realizing a purpose of assisting the ligating clip. The turning mechanism is provided with a flushing valve communicated with the cavity tube, when flushing, a flushing can be made by only opening the flushing valve. Disassembly and reassembly are not needed during cleaning and disinfection, thereby reducing working intensity and skill requirements of medical workers, avoiding damage, missing, mixed assembly and wrong assembly of parts caused due to frequent disassembly, assembly and cleaning, and preventing a risk of accidental touching triggering when the ligating clip is being assembled and fails to reach a clipping position.

Reference numerals in the figures are as follows: 1. Fixing Handle; 2. Triggering Handle; 3. Turing Mechanism; 4 Cavity Tube; 5. Thimble; 6. Joint Screw; 7. Rolling ball Groove; 8. Locking Key; 9. Crook Stop; 11. First Cavity; 12. Second Cavity; 13. Back Cover; 14. Locking Key Hole; 15. Pin Groove; 21. Annular Force Applying Part; 22. Lock Hole; 31. Flushing Valve; 32. Ridge; 33. Rolling ball; 34. Pin; 35. Protective Cover; 41. Mounting Head; 42. Spring Limiter; 51. Tip; 52. Needle Bar; 53. Tail; 54. Resetting Spring; 55. Steel Ring; 56. Coaxial Positioning Structure; 81. Locker; 82. Key Position Marble; 91. Spring-Snap Connection Configuration; 92 Screwing-Snap Connection Configuration.

DETAILED DESCRIPTION

In the following, a detailed and complete description of the present disclosure will be made in combination with specific embodiments with reference to the drawings.

Referring to FIGS. 1-9, the present disclosure provides a disassembly-free and flushable clip applier (called "applier" for short hereafter), which is connected with a ligating clip and used for auxiliary application of the ligating clip, and it includes: a fixing handle 1 and a triggering handle 2, the fixing handle 1 being hinged with the triggering handle 2; a cavity tube 4 rotatably sleeved on the fixing handle 1, a front end of the cavity tube 4 being provided with a mounting head 41 which is configured for detachably connecting the ligating clip, a diameter of a tail end of the cavity tube 4 being larger than a diameter of the front end of the cavity tube 4; a turning mechanism 3 sleeved at the tail end of the cavity tube 4, the turning mechanism 3 being provided with a flushing valve 31 which is communicated with the cavity tube 4 for flushing; and a thimble 5 axially infixed into the cavity tube 4 and reciprocating along an axial direction of the cavity tube 4, the thimble 5 including a tip 51 and a tail 53, the tail 53 being connected with the triggering handle 2 and the tip 51 being configured for pushing the ligating clip mounted on the mounting head 41 to move. During use, the fixing handle 1 is held and the triggering handle 2 is buckled by fingers, the thimble 5 can be driven to move in the cavity tube 4 by the triggering handle 2, thereby driving the ligating clip connected with the cavity tube 4 to move and realizing a purpose of assisting the ligating clip. The turning mechanism 3 is provided with a flushing valve 31 communicated with the cavity tube 4, when flushing, a flushing can be made by only opening a protective cover 35. Disassembly and reassembly are not needed during cleaning and disinfection, thereby reducing working intensity and skill requirements of medical workers, avoiding damage, missing, mixed assembly and wrong assembly of parts caused due to frequent disassembly, assembly and cleaning, and preventing a risk of accidental touching triggering when the ligating clip is being assembled and fails to reach a clipping position.

Figure 2:
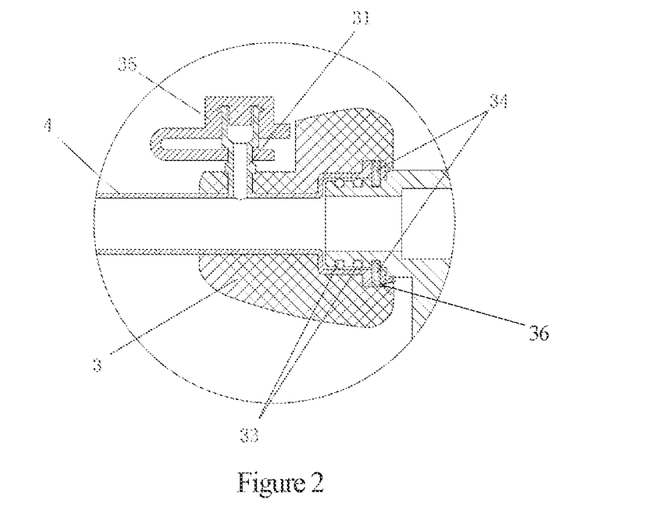
FIG. 2 is a schematic diagram of an internal structure at A in FIG. 1.
Figure 3:
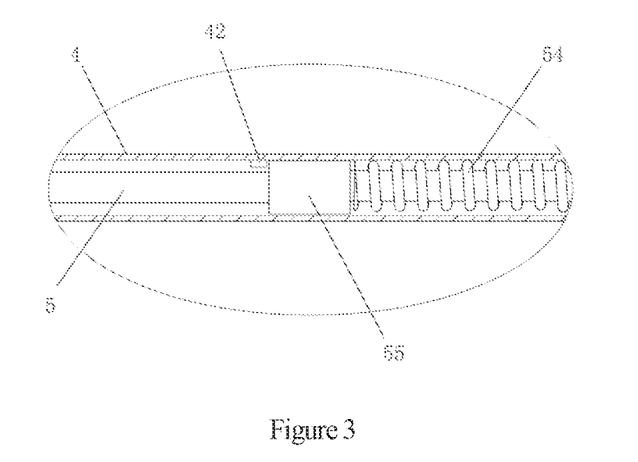
FIG. 3 is a schematic diagram of an internal structure at B in FIG. 1.
Figure 6:
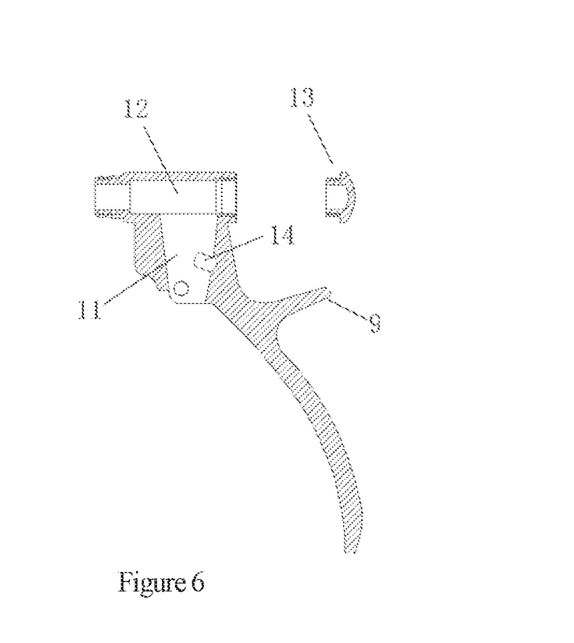
FIG. 6 is a sectional view of the fixing handle according to the present disclosure.

In an embodiment of the present disclosure, a first cavity 11 and a second cavity 12 are provided in the fixing handle 1. The first cavity 11 is communicated with the second cavity 12, the triggering handle 2 is arranged in the first cavity 11 and hinged with the fixing handle 1 through a joint screw 6; and the second cavity 12 is communicated with the cavity tube 4 for resetting the thimble 5. The first cavity 11, the second cavity 12 and the cavity tube 4 are all communicated, and an interior of the cavity tube 4 can be cleaned only by opening the protective cover 35 during flushing. The triggering handle 2 and the fixing handle 1 are hinged by the joint screw 6, with a simple connection mode and firm structure. A tail end of the second cavity 12 is connected with a back cover 13.

The diameter of the tail end of the cavity tube 4 being larger than the diameter of the front end of the cavity tube 4, and the tail end of the cavity tube 4 is provided with a pin hole 34 and the fixing handle 1 is provided with a rolling ball groove 7 and a pin groove 15. An inner wall of the cavity tube 4 is matched with the rolling ball groove 7 through the rolling ball 33 to realize a 360° rotation, and the cavity tube 4 is axially limited by matching a pin 34 with the pin groove 15, and a spring limiter 42 is provided on an inner wall of the cavity tube 4. This structure has advantages of reversibility, low friction and high efficiency, in which wear is not easily caused to parts, thus improving the service life of the clip applier.

Figure 4:
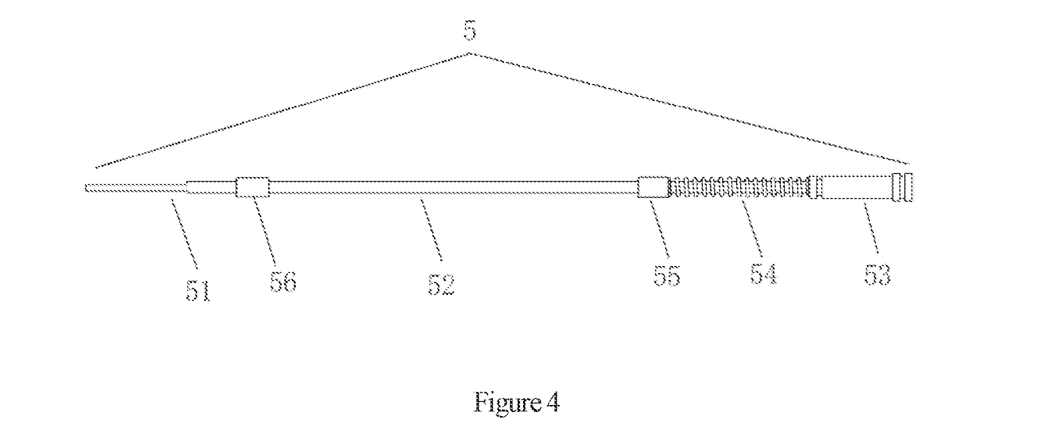
FIG. 4 is a schematic structural diagram of a thimble according to the present disclosure.

The thimble 5 further includes a needle bar 52 and a resetting spring 54. An end of the needle bar 52 is connected with the tip 51 through a coaxial positioning structure 56 attached to the inner wall of the cavity tube so that the tip 51 is in a central position of the cavity tube 4. The other end of the needle bar 52 is connected with the tail 53. A steel ring 55 is sleeved on an outer side of the needle bar 52 and a spring limiter 42 is provided on an inner cavity surface of the cavity tube 4. The steel ring 55 abuts against the spring limiter 42 of the cavity tube 4 for limiting. The resetting spring 54 is sleeved on the needle bar 52, and an end of the resetting spring 54 abuts against the tail 53 and the other end of the resetting spring abuts against the steel ring 55 for resetting the thimble 5. When the triggering handle 2 is buckled, the triggering handle 2 pushes the thimble 5 through a lever movement of the joint screw 6, which drives the thimble 5 to move along an axial center of the cavity tube 4 to a position beyond the front end of the cavity tube 4, thus realizing a clipping of the ligating clip; and at this time, under an action of the spring limiter 42 and the steel ring 55, the tail 53 compresses the resetting spring 54, and after the action is completed, the triggering handle 2 is released, and the resetting spring 54 drives the thimble 5 to reset without any manual resetting, thus saving effort during use.

Figure 8:
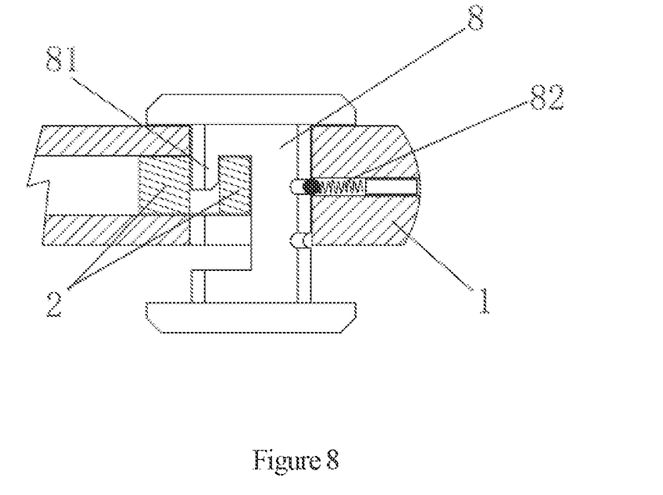
FIG. 8 is a schematic plan partial cross-sectional view of a locking key according to the present disclosure in a closed key position state.
Figure 9:
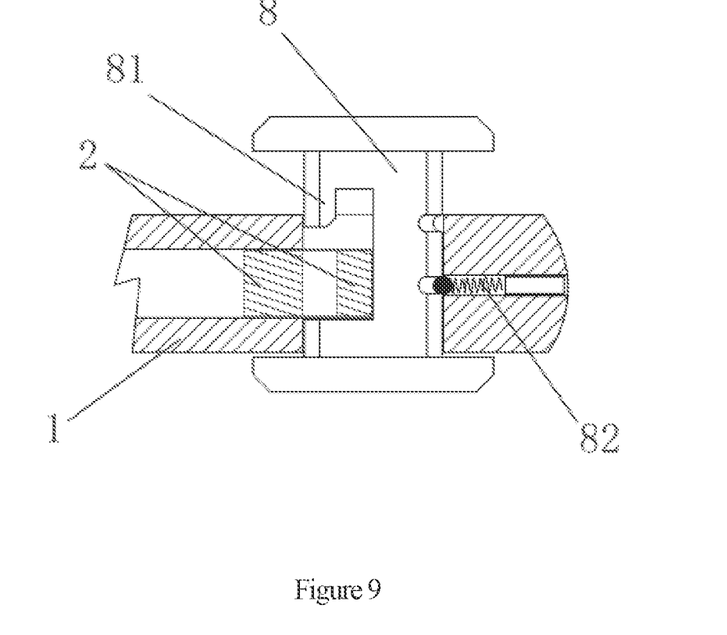
FIG. 9 is a schematic plan partial cross-sectional view of a locking key according to the present disclosure in an open key position state.
Figure 10:
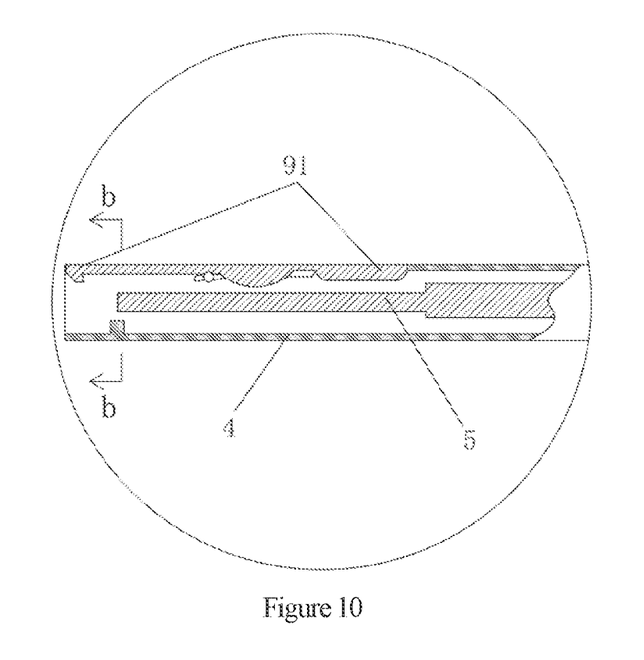
FIG. 10 is a schematic diagram of a spring-snap connection of a mounting head of the cavity tube according to the present disclosure.
Figure 11:
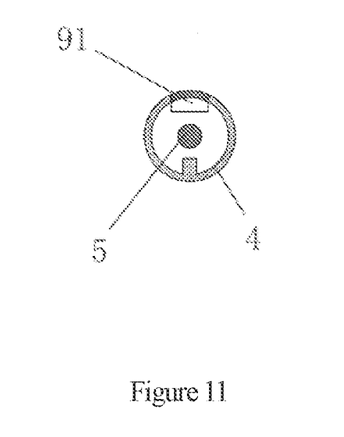
FIG. 11 is a sectional view taken at b-b in FIG. 10.
Figure 12:
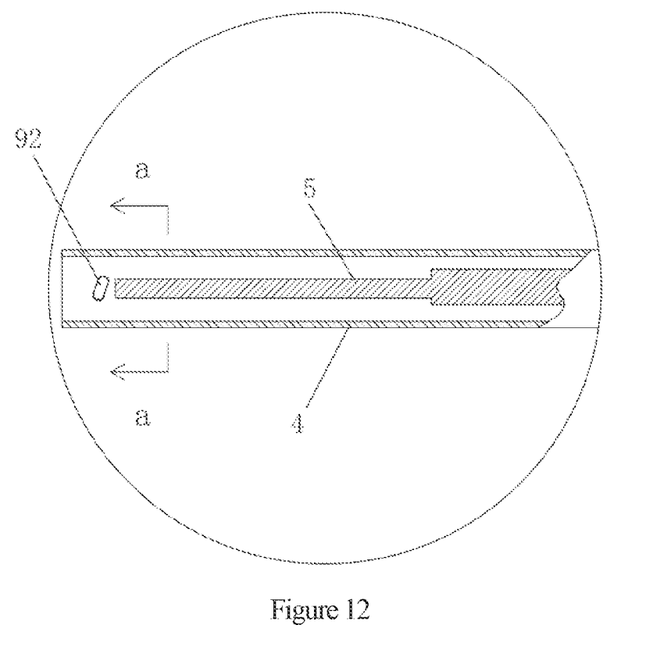
FIG. 12 is a schematic diagram of a screwing-snap connection of a mounting head of the cavity tube according to the present disclosure.
Figure 13:
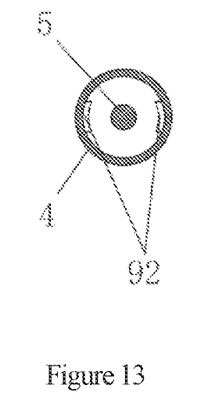
FIG. 13 is a sectional view at a-a in FIG. 12.

The clip applier further includes a locking key 8. Two sides of the fixing handle 1 are provided with locking key holes 14 mutually communicated with each other. The locking key 8 is movably arranged in the locking key holes 14. The locking key 8 is provided with a locker 81 and the triggering handle 2 is provided with a lock hole 22, and the locker 81 is matched with the lock hole 22 for controlling a rotation of the triggering handle 2. The locking key 8 can be movably arranged in the locking key hole 14, and when the locking key 8 is pushed, the locker 81 of the locking key 8 is matched with the lock hole 22 on the triggering handle 2 for limiting, with a simple structure. A locking side of the locking key 8 can be pushed to lock the locker 81 in the lock hole 22, and at this time, the locking key 8 locks the triggering handle 2, that is, it is in a locked state; and an unlocking side of the locking key 8 can be pushed, so that the locker 81 exits the lock hole 22, and at this time, the triggering handle 2 can move relative to the fixing handle 1, that is, it is in an unlocked state. A rear end of the locking key hole 14 on the fixing handle 1 is provided with a key position marble 82, and a side of the locking key 8 contacting with the key position marble 82 is provided with an adaptable groove for limiting a position of the locking key 8 in the locked or unlocked state. The locking key 8 is exposed on an end face of the fixing handle 1, so that the locking state and the unlocking state can be identified for a user to distinguish and use.

Figure 5:
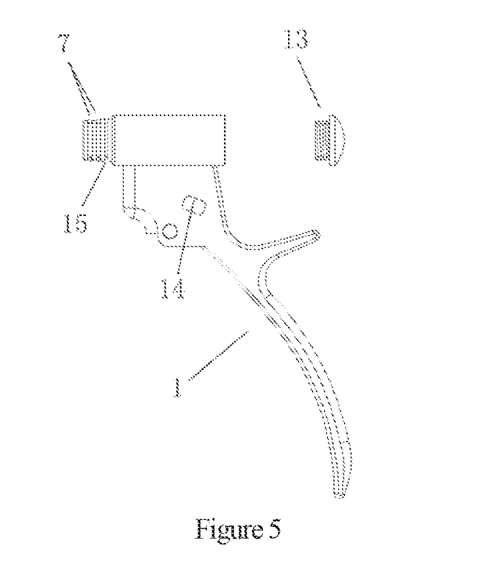
FIG. 5 is a schematic diagram describing an outline of a fixing handle according to the present disclosure.

The fixing handle 1 further includes a crook stop 9, which is arranged on a side of the fixing handle 1 away from the triggering handle 2 and is configured for a nonskid limiting of a crook of a palm.

Figure 1:
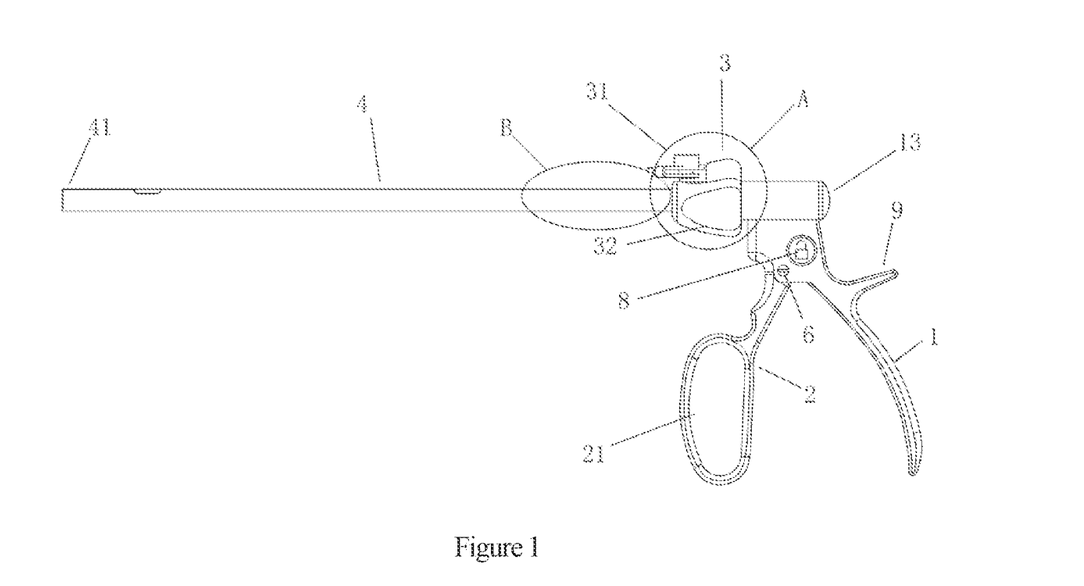
FIG. 1 is a schematic structural diagram of a disassembly-free and flushable clip applier according to the present disclosure.

The clip applier further includes a protective cover 35 which is detachably arranged on the flushing valve 31 for dustproof at the flushing valve 31 and is made of silica gel, which is of flexible material and has good sealing performance.

A plurality of ridges 32 are circumferentially provided on an outer side of the turning mechanism 3 for a single-finger dialing rotation.

A connection mode of the cavity tube 4 with the ligating clip is a spring-snap connection 91 or a screwing-snap connection 92. During a surgery, it is usually necessary to use a variety of ligating clips in cooperation with the clip applier, and the clip applier according to the present disclosure provides a variety of connection modes which are simple and convenient to disassemble and replace the ligating clips, thus improving efficiency.

Figure 7:
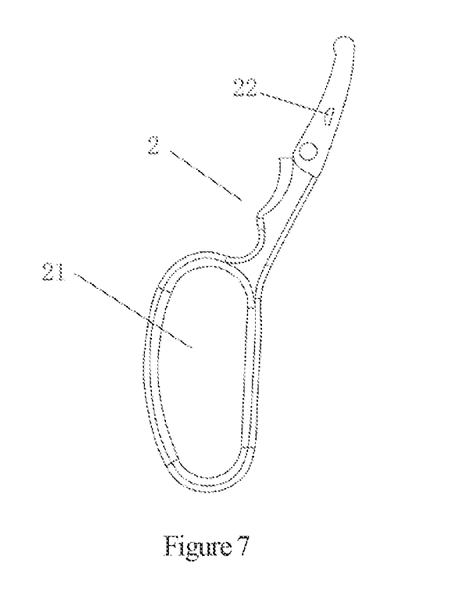
FIG. 7 is a schematic structural diagram of a triggering handle according to the present disclosure.

An end of the triggering handle 2 away from the thimble 5 is provided with an annular force applying part 21 for stably applying a force by a finger during use, and this closed annular structure can prevent the clip applier from slipping from the hand.

The above is only preferred embodiments of the present disclosure, which does not limit a protection scope of the present disclosure. Any equivalent transformation made with the specification of the present disclosure, which is directly or indirectly applied to other related technical fields, is included within the scope of the disclosure.

What is claimed is:

1. A disassembly-free and flushable clip applier connected with a ligating clip and used for auxiliary application of the ligating clip, comprising:
   a fixing handle and a triggering handle, the fixing handle being hinged with the triggering handle;
   a cavity tube, the cavity tube is hollow, a front end of the cavity tube being provided with a mounting head, the mounting head being configured for detachably connecting the ligating clip, a diameter of a tail end of the cavity tube being larger than a diameter of the front end of the cavity tube, the tail end of the cavity tube with a larger diameter then the front end of the cavity tube is directly sleeved on the fixing handle to cooperate with the fixing handle, realizing a 360° rotation and an axial limit and facilitating cleaning;
   a turning mechanism sleeved at the tail end of the cavity tube and rotatably connected with the fixing handle through a rolling ball, the turning mechanism being provided with a flushing valve, the flushing valve being communicated with the cavity tube for flushing; and
   a thimble axially infixed into the cavity tube and reciprocating along an axial direction of the cavity tube, the thimble comprising a tip and a tail, the tail being connected with the triggering handle and the tip being configured for pushing the ligating clip mounted on the mounting head of the cavity tube to move;
   wherein a first cavity and a second cavity are both provided in the fixing handle for facilitating cleaning, the first cavity being communicated with the second cavity, the triggering handle being arranged in the first cavity and hinged with the fixing handle through a joint screw; and
   the second cavity being communicated with the cavity tube for resetting the thimble;
   wherein the tail end of the second cavity being connected with a back cover, the disassembly-free and flushable clip applier further comprises a protective cover, and the protective cover is detachably arranged on the flushing valve, and the first cavity, the second cavity and the cavity tube are all communicated to facilitate flushing;
   wherein the protective cover is made of silica gel;
   wherein an interior of the cavity tube can be cleaned only by opening the protective cover during flushing and disassembly and reassembly are not needed during flushing.

2. The disassembly-free and flushable clip applier according to claim 1, wherein the tail end of the cavity tube is provided with a pin hole and the fixing handle is provided with a rolling ball groove and a pin groove, an inner wall of the cavity tube being matched with the rolling ball groove through the rolling ball to realize the 360° rotation and the cavity tube being axially limited by matching a pin with the pin groove.

3. The disassembly-free and flushable clip applier according to claim 1, wherein the thimble further comprises a needle bar and a resetting spring, an end of the needle bar being connected with the tip through a coaxial positioning structure attached to an inner wall of the cavity tube so that the tip is in a central position of the cavity tube, another end of the needle bar being connected with the tail, a steel ring being sleeved on an outer side of the needle bar and a spring limiter being provided on an inner cavity surface of the cavity tube, the steel ring abutting against the spring limiter of the cavity tube for limiting, the resetting spring being sleeved on the needle bar, and an end of the resetting spring abutting against the tail and another end of the resetting spring abutting against the steel ring for resetting the thimble.

4. The disassembly-free and flushable clip applier according to claim 1, further comprising a locking key, two sides of the fixing handle being provided with locking key holes mutually communicated with each other, the locking key being movably arranged in the locking key holes, the fixing handle being provided with a key position marble for limiting unlocking and locking positions of the locking key, the locking key being provided with a locker and the triggering handle being provided with a lock hole, and the locker being matched with the lock hole for controlling a rotation of the triggering handle.

5. The disassembly-free and flushable clip applier according to claim 1, wherein the fixing handle further comprises a crook stop, and the crook stop is arranged on a side of the fixing handle away from the triggering handle and is configured for a nonskid limiting of a crook of a palm during holding.

6. The disassembly-free and flushable clip applier according to claim 1, wherein a plurality of ridges is circumferentially provided on an outer side of the turning mechanism for a single-finger dialing rotation.

7. The disassembly-free and flushable clip applier according to claim 1, wherein a connection mode of the cavity tube with the ligating clip is a spring-snap connection or a screwing-snap connection.

8. The disassembly-free and flushable clip applier according to claim 1, wherein an end of the triggering handle away from the thimble is provided with an annular force applying part for stably applying a force by a finger and preventing slipping during use.

* * * * *